United States Patent [19]

Ulrich et al.

[11] Patent Number: 4,658,809
[45] Date of Patent: Apr. 21, 1987

[54] IMPLANTABLE SPINAL DISTRACTION SPLINT

[75] Inventors: Heinrich Ulrich, Ulm/Donau; Klaus Zielke, Bad Wildungen, both of Fed. Rep. of Germany

[73] Assignee: Firma Heinrich C. Ulrich, Ulm/Donau, Fed. Rep. of Germany

[21] Appl. No.: 583,131

[22] Filed: Feb. 24, 1984

[30] Foreign Application Priority Data

Feb. 25, 1983 [DE] Fed. Rep. of Germany ....... 3306657

[51] Int. Cl.⁴ .................................................. A61F 5/04
[52] U.S. Cl. ........................... 128/92 YM; 128/92 YF
[58] Field of Search .................. 128/69, 92 A, 92 ZZ, 128/92 YM, 92 YF

[56]  References Cited

U.S. PATENT DOCUMENTS

| 4,047,523 | 9/1977 | Hall | 128/69 |
| 4,386,603 | 6/1983 | Mayfield | 128/69 |
| 4,411,259 | 10/1983 | Drummond | 128/69 |

FOREIGN PATENT DOCUMENTS 3219575 12/1983 Fed. Rep. of Germany ........ 128/69
485739 12/1975 U.S.S.R. ................................. 128/69
654251 3/1979 U.S.S.R. ................................. 128/69
1022702 6/1983 U.S.S.R. ................................. 128/69

Primary Examiner—C. Fred Rosenbaum
Assistant Examiner—C. W. Shedd
Attorney, Agent, or Firm—Karl F. Ross; Herbert Dubno

[57] ABSTRACT

A spinal distraction apparatus has a distraction rod extending along an axis and having in turn a center part, a pair of end parts secured in, extending axially oppositely from, and rotatable about the axis relative to the center part, and a screwthread connection between each of the end parts and the center part. The screwthread connections are of opposite hand so that rotation of the center part in one direction moves the end parts axially toward each other and opposite rotation moves them axially apart. The end parts are axially nondisplaceable relative to the center part except on rotation of same about the axis. Respective anchors axially nondisplaceable on the end parts are adapted to be secured to respective vertebra. Formations between the anchors and the respective end parts prevent rotation of the end parts about the axis relative to the anchors.

11 Claims, 11 Drawing Figures

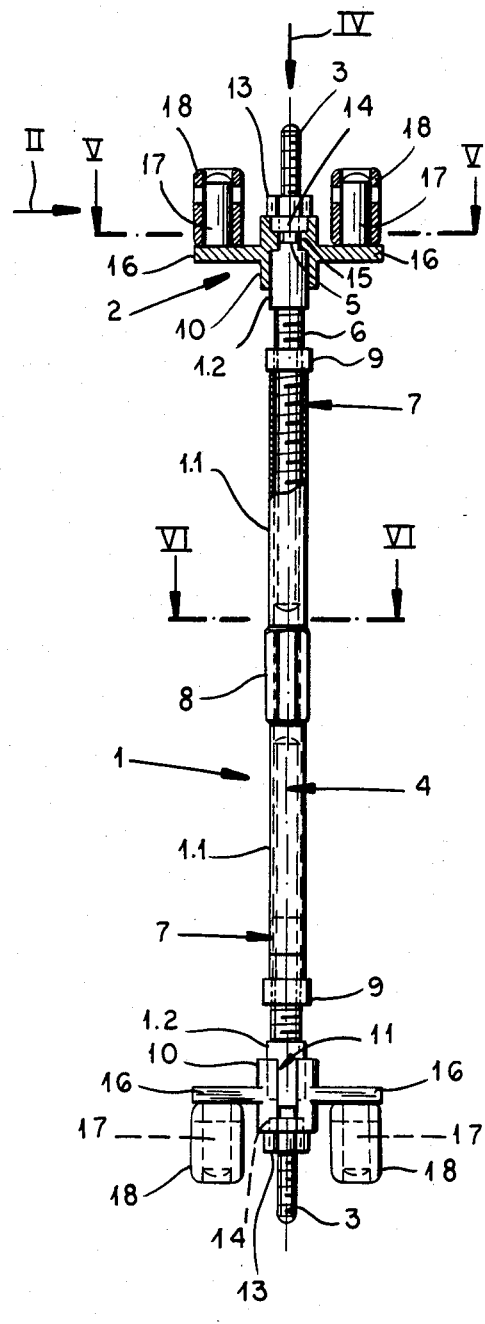
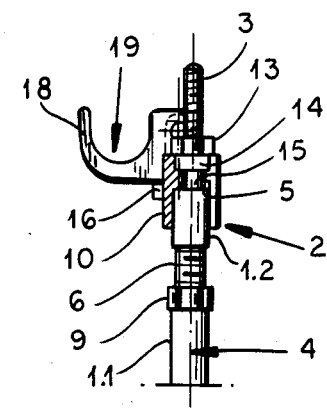
FIG.2
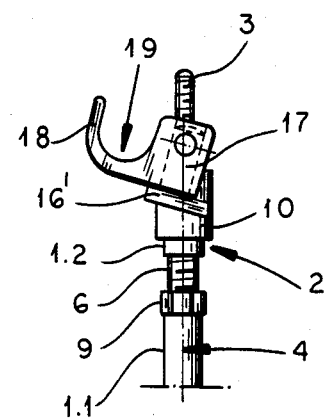
FIG.3
FIG.1

IMPLANTABLE SPINAL DISTRACTION SPLINT

FIELD OF THE INVENTION

The present invention relates to an implantable spinal distraction apparatus. More particularly this invention concerns such an apparatus or splint which is used to correct curvature of the spine.

BACKGROUND OF THE INVENTION

In commonly owned patent application Ser. No. 383,175 U.S. Pat. No. 4,433,677 issued Feb. 28, 1984 a distraction splint is disclosed having two like anchor screws extending along respective longitudinal screw axes and adapted to be anchored in the pelvis with their axes crossing. Each of the screws has a head formed with a transversely open recess centered on a respective transverse axis and with an annular array of teeth centered on and angularly equispaced about the respective transverse axis. A bolt extends through one of the recesses and is threaded in the other recess. Thus the bolt secures the heads together with the transverse axes coaxial and the teeth interengaged. Respective distraction rods each have one end braced on the respective screw and another end braced oppositely against a vertebra.

This device is relatively effective, but can only be used to stabilized a straightened spinal region, not to straighten one. Thus a separate straightening device is usually employed to straighten out the spine, whereupon the splint is attached. The splint itself is not used for the straightening operation as the distraction rod is only limitedly longitudinally extensible.

Such a straightening device is described in commonly owned patent application Ser. No. 383,272 (U.S. Pat. No. 4,433,677 issued Feb. 28, 1984. This device serves to straighten a spinal column having a succession of vertebrae extending along a nonstraight line lying generally in a plane and has an elongated bar lying generally in the plane of the line and having a pair of relatively longitudinally displaceable bar parts in turn having respective bar ends. A pair of connectors at the bar ends are secured to respective vertebrae of the succession. Respective pivots between the connectors and the respective ends define therebetween respective generally parallel axes transverse to the plane. A main abutment movable along and fixable on one of the parts and longitudinally engageable with the other of the parts serves for limiting relative longitudinal displacement of the parts toward each other. Thus the main abutment can be moved along the one part to increase the spacing between the ends and thereby can straighten the succession of vertebrae between the connectors.

It is also known from German Pat. No. 2,649,042 based on an application filed Oct. 28, 1976 by M. B. Ulrich to provide an implantable splint that constitutes part of the device that actually does the straightening, and that can be left in the patient after the spine is straightened to keep the hitherto curved portion of the spine straight, although it is noted of course that the term "straight" is relative only as virtually all parts of the spine are at least gently curved. This splint has a threaded rod that is bendable and extends through a succession of anchors secured to the vertebrae to be straightened. Another implement is employed to initially straighten the succession of vertebrae, with concomitant adustment of pairs of nuts on the threaded rod that flank the respective anchors. Once the desired straightness is established, the pairs of nuts are tightened against the respective anchors to lock in the set position. This system allows the patient to be closed up after surgery, but still entails considerable work for the initial straightening operation. In addition the rod or rods, which must be flexible in order to follow the original curved line of the anchors, cannot be very rigid, so that occasionally the spine will at least partially revert to its initial nonstraight position.

Another principal disadvantage of all these systems is that they are only effective at exerting longitudinal tension. They do not exert any compression at all, and in fact can come unhooked relatively easily if, for instance, the spine is momentarily bent forward. In addition it is impossible to vary the length of the standard distraction rod once it has been installed. Length adjustment of any significant or useful amount is only possible by swapping the implanted rod with one of a different length, a surgical procedure that is obviously complex and normally considered excessive. Thus the known implants are not usable on a nonadult patient, as they cannot be adjusted as the patient grows.

OBJECTS OF THE INVENTION

It is therefore an object of the present invention to provide an improved implantable spinal distraction apparatus.

Another object is the provision of such an implantable spinal distraction apparatus which overcomes the above-given disadvantages, that is which can be exert compressive as well as distractive forces and which can also be used for the initial distraction of the spine.

A further object is to provide such a splint which can be adjusted relatively easily once it is implanted so that it can be installed in a growing child and can be lengthened as needed.

SUMMARY OF THE INVENTION

A spinal distraction apparatus according to this invention has a distraction rod extending along an axis and having in turn a center part, a pair of end parts secured in, extending axially oppositely from, and rotatable about the axis relative to the center part, and a screwthread connection between at least one of the end parts and the center part. Thus rotation of the center part relative to the one end part axially relatively displaces the one end part and the center part. The end parts are axially nondisplaceable relative to the center part except on rotation of same about the axis. Respective axially nondisplaceable members secured on the end parts are adapted to be connected to respective vertebrae. Formations between the anchors and the respective end parts prevent rotation of the end parts about the axis relative to the members. Connecting means is provided for connecting the members to selected vertebrae.

According to this invention there is normally another such screwthread connection between the other end part and the center part. The screwthread connections are of opposite hand so that rotation of the center part in one direction moves the end parts axially toward each other and opposite rotation moves them axially apart.

With such an arrangement it is therefore possible to adjust the length of the rod merely by gripping and turning the center part. Even if the device has been implanted in a person, the incision necessary to do this is minor so that readjustment of the implant is possible, even if desired to shorten it as can be needed in some circumstances, as for instance in the treatment of kyphosis. As a result the apparatus of this invention is ideal for use in growing children, since it provides the corrective advantage of an implant without subjecting the scoliotic child to the risk of repeated major surgery for adjustment of the implant. The apparatus can also be mounted laterally or even ventrally on the spine and as mentioned can be tensioned if desired, depending on the type of correction needed.

According to another feature of this invention the center part has tubular internally threaded ends and the end parts are engaged in the respective ends and are externally threaded. This style of construction makes it possible for the rod to almost double in length if necessary, making it possible for it to be used for initial distraction and then subsequent readjustment over many years in a growing patient. What is more, such a construction is very rugged. It can be provided with lock nuts threaded on the end parts and axially engageable with the center-part ends so that the set length can be fixed.

The formation according to this invention include respective radially outwardly projecting noses on the end parts and respective radially inwardly open recesses on the members receiving the respective noses. In fact each of the members normally has an axially throughgoing passage and each of the end parts has an axially outwardly projecting threaded stem extending through the respective passage. Each of the members is formed with a groove opening radially from the respective passage and of a width sufficient to radially pass the respective threaded stem and each is formed in the passage with a central region defining a small open cross section and to each axial side of this central region with a pair of enlarged regions. Each end part fits snugly into one of the respective enlarged regions and the respective stem is provided with a nut fitting snugly into the other respective enlarged region. Thus this groove can form the recess in which the nose engages, serving two functions. Such construction makes it possible to assemble the apparatus once the members have been properly fixed on the respective vertebra, without fear of it coming apart postoperatively.

For compression of a corrected kyphotic spinal chord, each member is provided with the connecting means in the form of an integral screw adapted to be screwed into the respective vertebra. Thus the rod can be shortened for the necessary stabilization.

For correcting spinal deformities in children each anchor is formed with a pair of radially oppositely extending arms each provided with an axially outwardly directed pin. These members each further have respective axially outwardly open hooks pivoted on the pins, the pivoting allowing some freedom of motion to remain in the spine. These pins can extend parallel to the rod axis or dorsally backward at an angle which enhances hook engagement with the vertebrae, e.g. of up to 20° thereto. In addition the pins lie slightly ventrally forward of the rod axis.

DESCRIPTION OF THE DRAWING

The above and other features and advantages will become more readily apparent from the following, reference being made to the accompanying drawing in which:

FIG. 1 is a partly sectional dorsal view of the splint according to this invention;

FIG. 2 is a side view of the upper end of the splint of FIG. 1 but with some parts removed for clarity of view;

FIG. 3 is a view like FIG. 2 of a variation on the system of FIG. 1;

SPECIFIC DESCRIPTION

Figure 4:
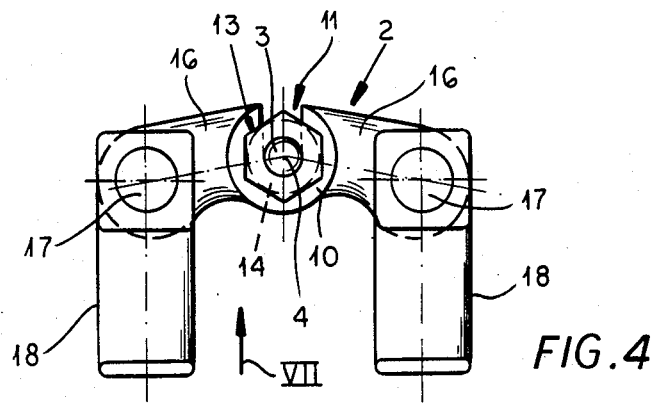
FIG. 4 is a large-scale top view of the splint of FIG. 1.
Figure 5:
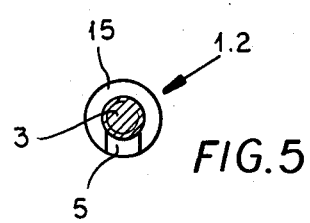
FIG. 5 is a section through the distraction rod taken along the plane indicated at V—V in FIG. 1.
Figure 6:
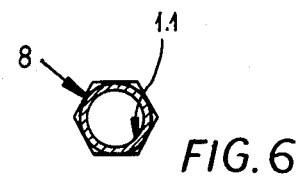
FIG. 6 is a section taken along plane VI—VI of FIG. 1.

As seen in FIGS. 1, 2, 4–7, and 8a the distraction apparatus according to this invention basically comprises a distraction rod 1 extending along an axis 4 and basically formed of a tubular center part 1.1 and a pair of end parts 1.2. Threaded extensions 3 of the end parts 1.2 extend through members 2 that are adapted to be connected to respective vertebra at opposite ends of a curved section of spine to be straightened.

The center part 1.1 is formed in each of its axially opposite ends with an internal screwthread 7 into which is screwed a complementary thread 6 of the respective end part 1.2. The screwthreads 7 are of opposite hand so that rotation of the center part 1.1 in one direction about the axis 4 will axially elongate the rod 1 and opposite rotation will axially shorten it. Centrally the part 1.1 has a hexagonal-section faceted region 8 suitable for engagement by an open-end wrench for turning this center part 1.1 relative to the end parts 1.2. In addition lock nuts 9 are threaded on the end parts 1.2 to lock them against rotation by screwing these nuts 9 down on the ends of the center part 1.1 once a given setting is to be established and maintained.

Figure 8A:
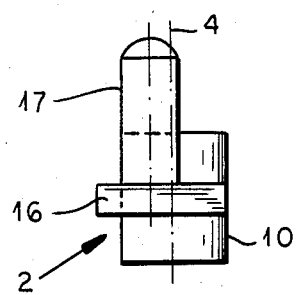
FIG. 8a is a side view of the structure shown in FIG. 7.

The anchors 2 each have a basically cylindrical body 10 centered on the axis 4 and traversed by the respective threaded extension 3, and a pair of radially oppositely projecting platforms or extensions 16 each formed with a pin 17 projecting parallel to the axis 4 away from the center part 1.1. Each of these pins 17 carries a respective hook 18 having a recess 19 that opens axially outward, that is away from the center part 1.1, so it can be engaged in a spongy process or part of the respective vertebra. In addition as best seen in FIGS. 4 and 8a, the pins 17 lie ventrally forward of the axis 4, ensuring that the hooks 18 will effectively engage the spinal pedicles.

Figure 8B:
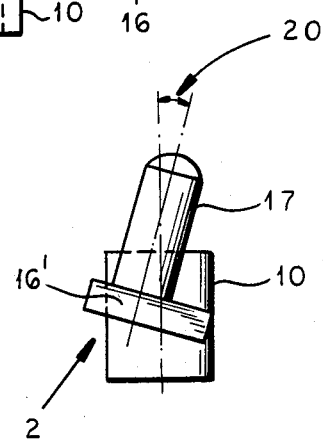
FIG. 8b is a view like FIG. 8a of a variation on the system.

The platforms 16 can also be tipped as shown at 16' in FIGS. 3 and 8b so that the pins 17 extend at an angle 20 of up to 20°, here 15°, to the axis 4. This is useful in correcting a severe deformity.

Figure 7:
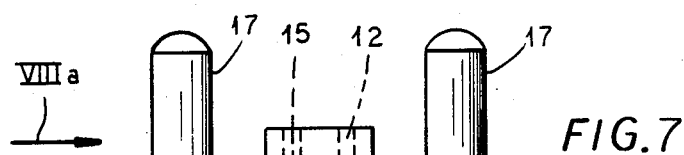
FIG. 7 is a side view of the structure shown in FIG. 4 but with some parts removed for clarity of view.

The body 10 of each member 2 is formed as best seen in FIGS. 2 and 7 with a radially and dorsally open slot 11 of a width slightly greater than the diameter of the respective extension 3 so that same can be fitted radially into it. The axially throughgoing passage thus formed in the body 10 has a central web 15 flanked by a pair of axially oppositely open and radially enlarged cylindrical regions 12 that are centered on the axis 4. The enlarged region 12 turned axially inward snugly receives the end 15 of the respective end part 1.2 and the opposite region 12 snugly receives a cylindrical collar 14 on a nut 13 threaded on the respective extension 3. In addition each part 1.2 is formed with a radially extending nose or projection 5 that snugly fits between the sides of the slot 11 to prevent relative rotation of the respective parts 1.2 and 2.

It is therefore possible to fit the threaded part 3 of an end part 1.2 radially into the groove 11, then screw down the nut 13 to lock each end part against movement along the axis 4 relative to the member 2 or angularly about the axis 4 relative thereto. The distraction apparatus can therefore be assembled in situ, after the hooks 18 have been anchored.

Figure 9:
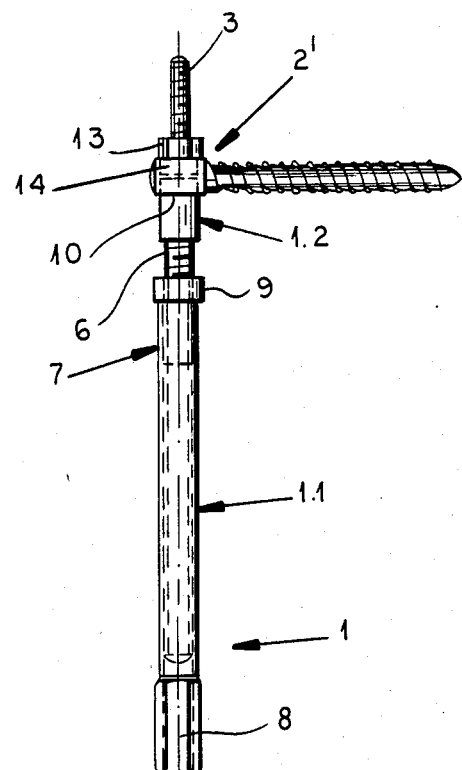
FIG. 9 is a side view of another distraction apparatus according to this invention.
Figure 10:
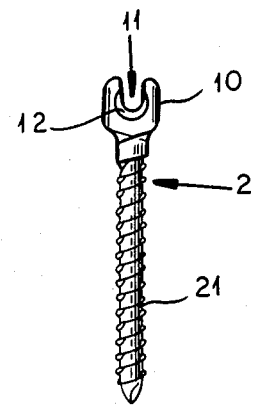
FIG. 10 is a top view of the anchor of the apparatus of FIG. 9.

FIGS. 9 and 10 further show how the body 10 of each member 2' can be provided with a radially extending screw 21 that is opposite the groove 11, replacing the arms 16 and pins 17. Otherwise the body 10 of FIGS. 9 and 10 is shaped identically to that of FIGS. 1 through 8.

In use the members 2 or 2' are fixed in the respective vertebra with the slots 11 opening dorsally. One of the end pieces 1.2 is then fitted into one of the slots and the respective nut 13 is snugged, care being taken to fit the respective nose 5 into the slot 11 to prevent relative rotation of this end part 1.2 and the respective member 2 or 2'. The center part 1.1 is then rotated to fit the other threaded end 3 through the other member 2 or 2' and the other nut 13 is snugged. At this time, then, both of the nuts 13 can be tightened somewhat more.

A wrench is then fitted to the faceted central region 8 of the center part 1.1 and this element is rotated about the axis 4 in a direction to push the two members 2 or 2' apart. Such rotation is continued until the desired distraction is obtained, at which time the two lock nuts 9 are backed inward on the end parts 1.2 against the ends of the part 1.1 to stabilize the entire assembly, which can be left implanted in the patient. For opposite correction the center part 1.1 is rotated oppositely to shorten the rod 1, of course.

At a later data it is relatively easy to further lengthen the assembly simply by making three small incisions to expose the faceted region 8 and the two lock nuts 9, and the center part 1.1 can be again rotated until the new distraction is obtained.

Since the threaded regions of the end parts 1.1 are relatively long, it is possible to almost double the overall length of the distraction rod 1, providing more than enough adjustability for virtually any circumstance. Thus the same apparatus can be used to effect the initial distraction, to splint the spine at the initial setting, and even to make further increased distractions as the patient grows. What is more, the rod 1 is solidly fixed to the members 2 and 2' so that it cannot become unhooked, even if the patient is subject to quite some violence. Hence the system is ideal for use in children where growth can be accommodated and an extremely strong structure is needed.

What is more the same arrangement can be provided to correct different kinds of spinal curvature, so that a surgery department need not stock a whole set of different devices. Due to the size variation possible, the department also need not stock a whole range of different sizes either.

We claim:

1. A spinal distraction apparatus comprising:
    a distraction rod extending along an axis and having a center part,
    a pair of end parts secured to the center part, extending axially oppositely from the center part, and rotatable about the axis relative to the center part, the center part being exposed between the end parts, and
    respective screwthread connections of opposite hand between the end parts and the center part, whereby rotation of the center part about the axis in one direction relative to the end parts axially relatively displaces the end parts away from each other and from the center part and rotation of the center part in the opposite direction relative to the end parts axially relatively displaces the end parts toward each other, the end parts being axially nondisplaceable relative to the center part except on rotation of same about the axis;
    respective members secured axially nondisplaceable on the end parts and adapted to be connected to respective vertebrae;
    formations between the members and the respective end parts preventing rotation of the end parts about the axis relative to the members; and connection means for connecting said members with selected vertebrae.

2. The spinal distraction apparatus defined in claim 1 wherein the center part has tubular internally threaded ends and the end parts are engaged in the respective ends and are externally threaded.

3. The spinal distraction apparatus defined in claim 2, further comprising lock nuts threaded on the end parts and axially engageable with the center-part ends.

4. The spinal distraction apparatus defined in claim 1 wherein the formations include respective radially outwardly projecting noses on the end parts and respective radially inwardly open recesses in the members for receiving the respective noses.

5. The spinal distraction apparatus defined in claim 1 wherein each of the members has an axially throughgoing passage and each of the end parts has an axially outwardly projecting threaded stem extending through the respective passage.

6. The spinal distraction apparatus defined in claim 5 wherein each of the members is formed with a groove opening radially from the respective passage and of a width sufficient to radially pass the respective threaded stem, the members further each being formed in the passage with a central region defining a small open cross section and to each axial side of this central region with a pair of enlarged regions, each end part fitting snugly into one of the respective enlarged regions and the respective stem being provided with a nut fitting snugly into the other respective enlarged region.

7. The spinal distraction apparatus defined in claim 6 wherein the formations include respective radially outwardly projecting noses on the end parts engaged radially in the grooves of the respective members.

8. The spinal distraction apparatus defined in claim 1 wherein said connection means is a screw adapted to be screwed into the respective vertebra.

9. The spinal distraction apparatus defined in claim 1 wherein each members is formed with a pair of radially oppositely extending arms each provided with a pin which receives a connection means in the form of an open hook, pivotable on the pin, for engaging said vertebae.

10. The spinal distraction apparatus defined in claim 9 wherein the pins are set at an angle so as to enhance hook engagement with said vertebrae.

11. The spinal distraction apparatus defined in claim 9 wherein the pins are offset from the rod axis.

* * * * *